US006341605B1

(12) United States Patent
Ohki et al.

(10) Patent No.: US 6,341,605 B1
(45) Date of Patent: Jan. 29, 2002

(54) INHALANT MEDICATOR

(75) Inventors: Hisatomo Ohki; Shigemi Nakamura; Kazunori Ishizeki; Yoshiyuki Yazawa, all of Gunma; Akira Yanagawa, Yokohama, all of (JP)

(73) Assignees: Unisia Jecs Corporation, Atsugi; Dott Limited Co., Yokohama, both of (JP)

( * ) Notice: Subject to any disclaimer, the term of this patent is extended or adjusted under 35 U.S.C. 154(b) by 0 days.

(21) Appl. No.: 09/355,737

(22) PCT Filed: Jan. 22, 1999

(86) PCT No.: PCT/JP99/00245

§ 371 Date: Aug. 4, 1999

§ 102(e) Date: Aug. 4, 1999

(87) PCT Pub. No.: WO99/39760

PCT Pub. Date: Aug. 12, 1999

(30) Foreign Application Priority Data

Feb. 5, 1998 (JP) ............................. 10-039674

(51) Int. Cl.⁷ ....................... A61M 16/00; A61M 15/00; B05D 7/14; B65D 83/06
(52) U.S. Cl. ...................... 128/203.15; 128/203.12; 128/203.21; 128/203.24
(58) Field of Search ................. 128/203.12, 203.15, 128/203.21, 203.24

(56) References Cited

U.S. PATENT DOCUMENTS

| 3,502,100 A | * | 3/1970 | Jonson .................. 137/501 |
| 3,837,341 A | * | 9/1974 | Bell ..................... 128/203.15 |
| 3,906,950 A | * | 9/1975 | Cocozza ................ 128/203.15 |
| 4,570,630 A | * | 2/1986 | Elliot et al. ............ 128/203.15 |
| 4,724,869 A | | 2/1988 | Carter |
| 5,165,392 A | | 11/1992 | Small, Jr. |

(List continued on next page.)

FOREIGN PATENT DOCUMENTS

| EP | 0 387 222 | 9/1990 | |
| EP | 0549299 A2 | * 6/1993 | ............ 128/206.12 |
| EP | 0 796 628 | 9/1997 | |
| JP | 8-47531 | 2/1996 | |

OTHER PUBLICATIONS

McPherson et al, Respiratory Therapy Equipment, 2ed., Gas Physics pp. 22–29, Dec. 1981.*

U.S. application No. 09/155,248, Ohki et al., filed Sep. 1998*

U.S. application No. 09/355,759, Ohki et al., filed Aug. 1999.*

*Primary Examiner*—John G. Weiss
*Assistant Examiner*—Joseph F. Weiss, Jr.
(74) *Attorney, Agent, or Firm*—Foley & Lardner

(57) ABSTRACT

An inhalant medicator comprises a medicator body formed at one axial end with a capsule housing hole and at another axial end with an inhalant port, an inflow air passageway having an axial inflow passage extending in an axial direction of the medicator body and a first pin insertion hole extending in a radial direction of the medicator body for communicating the capsule housing hole with the atmosphere, an outflow air passageway having an outflow passage extending in the axial direction of the medicator body and a second pin insertion hole extending in the radial direction of the medicator body for communicating the capsule housing hole with the inhalant port, and a boring tool having pins insertable toward a capsule through the first and second insertion holes for pricking holes in the capsule accommodated in the capsule housing hole with the pins. Also provided is a flow-constriction orifice (15, 15; 24A, 24A; 37, 37, 38, 38; 24C, 24C; 23C, 23C; 15', 15') disposed in at least one of the inflow and outflow air passageways and having an orifice size less than a flow passage area of each of the holes H.

7 Claims, 11 Drawing Sheets

U.S. PATENT DOCUMENTS

| | | | |
|---|---|---|---|
| 5,331,953 A | * 7/1994 | Andersson et al. | 128/200.14 |
| 5,337,740 A | * 8/1994 | Armstrong et al. | 128/203.12 |
| 5,351,683 A | * 10/1994 | Chiesi et al. | 128/203.12 |
| 5,379,763 A | * 1/1995 | Martin | 128/203.15 |
| 5,394,868 A | * 3/1995 | Ambrosio et al. | 128/203.15 |
| 5,529,059 A | * 6/1996 | Armstrong et al. | 128/203.15 |
| 5,619,985 A | * 4/1997 | Ohki et al. | 128/203.21 |
| 5,647,349 A | * 7/1997 | Ohki et al. | 128/203.15 |
| 5,715,811 A | 2/1998 | Ohki et al. | |
| 5,727,546 A | * 3/1998 | Clarke et al. | 128/203.15 |
| 5,752,505 A | * 5/1998 | Ohki et al. | 128/203.15 |
| 5,810,004 A | 9/1998 | Ohki et al. | |
| 5,899,202 A | 5/1999 | Ohki et al. | |
| 5,901,703 A | 5/1999 | Ohki et al. | |
| 5,921,236 A | 7/1999 | Ohki et al. | |
| 5,989,217 A | 11/1999 | Ohki et al. | |
| 5,996,577 A | 12/1999 | Ohki et al. | |
| 6,009,868 A | * 1/2000 | Nilson | 128/200.18 |

* cited by examiner

INHALANT MEDICATOR

TECHNICAL FIELD

The invention relates to an inhalant medicator suitable to prescribe granulated medicines toward within lungs of a patient by way of breathing action of the patient.

BACKGROUND ART

Generally, there are two typical medications of prescribing granulated medicines toward within lungs of an asthmatic patient, that is, one being a medication that the granulated medicines are inhaled by way of a liquid aerosol atomizer, and the other being an inhalation treatment that very fine granular medicines encapsulated in a capsule, such as granules each having a particle diameter ranging from 5 $\mu m$ to 10 $\mu m$, are inhaled by breaking through the capsule. Of these medications for an asthmatic patient, an inhalant medicator, used for the latter inhalation treatment where encapsulated granulated medicines are inhaled, has been disclosed in Japanese Patent Provisional Publication No. 8-47531.

The conventional inhalant medicator disclosed in the Japanese Patent Provisional Publication No. 8-47531 is generally comprised of a medicator body equipped at one axial end with a capsule housing area and at the other axial end with an inhalant port, an inflow air passageway having an axial inflow passage extending in the axial direction of the medicator body and a pin insertion channel extending in a radial direction of the medicator body for communicating the capsule housing area with the atmosphere, an outflow air passageway having an outflow passage extending in the axial direction of the medicator body and a pin insertion channel extending in the radial direction of the medicator body for communicating the capsule housing area with the inhalant port, and a boring tool having pins insertable toward the capsule through the respective pin insertion channels for breaking through the capsule accommodated in the capsule housing area.

In conventional inhalant medicator, when breaking through a capsule accommodated in the medicator body by way of a boring tool, a hole necessary to secure a required area of a flow passage to be created between the interior of the capsule and the pin insertion hole is formed in the capsule by inserting the pins toward the capsule along the respective pin insertion channels and by pricking or punching holes in the capsule with the pins.

Hereunder briefly explained is the inhalation treatment achieved by the previously-noted inhalant medicator. First of all, as a preparatory operation of the inhalant medication, a capsule filled with granular medicines is enclosed or fitted in the capsule housing area. Under this condition, the pins of the boring tool are moved in the respective pin insertion channels and guided towards the capsule. This permits the pins to penetrate or pierce the capsule in the radial direction of the capsule, thus forming holes pierced in the capsule and communicated with the respective pin insertion channels. Thereafter, the patient draws his or her breath while taking the inhalant port in his or her mouth in order to dose the patient with the granulated medicines stored in the capsule. This produces air flow through the axial inflow passage and the pin insertion channel included in the inflow air passageway toward within the capsule. The air flow agitates the granular medicines stored in the capsule, and flows out of the capsule together with the agitated granular medicines. The mixture of the incoming air and the granular medicines is then carried into the inhalant port through the pin insertion channel and the outflow passage included in the outflow air passageway. In this manner, the granular medicines flowing out of the capsule can be inhaled into the lungs of the patient.

In conventional inhalant medicator as discussed above, the formation of holes is achieved by punching or piercing holes in the capsule with pins. Therefore, there are slight fluctuations in hole sizes when forming holes in the capsule. Such slight fluctuations of the hole size result in variations in the fluid-flow passage area between the interior of the capsule and the pin insertion hole. A flow velocity and a flow rate of the air flowing through the internal space of the capsule are both regulated depending on the flow passage area of the hole penetrated by the pin. For the reasons set out above, during medication with a granular medicine having a strong condensation property, there is a problem of unstable dispersion of the granular medicine, thus preventing the granular medicine from being inhaled toward within lungs of a patient stably and satisfactorily at all times where medications are repeatedly made with medicines of different condensation properties.

It is, therefore, in view of the previously-described disadvantages of the prior art, an object of the present invention to provide an inhalant medicator which is capable of stably dispersing granulated medicines, while satisfactorily keeping a specified flow velocity and a specified flow rate of air flowing through the interior of a capsule pierced during medication.

DISCLOSURE OF THE INVENTION

In order to accomplish the aforementioned and other objects, according to the invention as claimed in claim 1, an inhalant medicator comprises a medicator body formed at one axial end with a capsule housing area and at another axial end with an inhalant port, an inflow air passageway having an inflow passage extending in an axial direction of the medicator body and a first pin insertion channel extending in a radial direction of the medicator body for communicating the capsule housing area with the atmosphere, and an outflow air passageway having an outflow passage extending in the axial direction of the medicator body and a second pin insertion channel extending in the radial direction of the medicator body for communicating the capsule housing area with the inhalant port, a boring tool having pins insertable toward a capsule through the first and second insertion channels for pricking holes in the capsules accommodated in the capsule housing area with the pins, and a flow-control orifice means disposed in a first air passageway of the inflow and outflow air passageways and having a flow passage area less than a flow passage area of each of the channels and less than a flow passage area of a second air passageway of the inflow and outflow air passageways. In the inhalant medicator made according to the invention defined in claim 1, the flow velocity and the flow rate of air flowing through the inflow air passageway, the capsule and the outflow air passageway can be adjusted or controlled by the flow-control orifice means having the flow passage area less than the flow passage area of each of the holes pricked or pierced in the capsule with the pins and less than the flow passage area of the second air passageway. Thus, the air of a specified flow velocity and a specified flow rate is able to stably and satisfactorily flow through the interior of the capsule, irrespective of fluctuations in the hole size of each of the holes pricked in the capsule.

According to the invention as claimed in claim 2, in order to provide the flow-control orifice means of the inhalant medicator, one air passageway of the inflow and outflow air passageways is formed as a flow-constriction passageway having a flow passage area less than the flow passage area of each of the holes pricked in the capsule with the pins. In the inhalant medicator made according to the invention defined in claim 2, the flow-constriction passage, having the flow passage area less than the flow passage area of each of the holes pricked in the capsule and less than the flow passage area of the second air passageway, is able to effectively adjust or control the flow velocity and the flow rate of the air flowing through the interior of the capsule.

According to the invention as claimed in claim 3, an orifice plate is fitted to the medicator body and located in at least one of the inflow and outflow air passageways, and the flow-control orifice means of the inhalant medicator is constructed by an orifice, formed in the orifice plate in a manner so as to communicate with the at least one of the inflow and outflow air passageways to control the air flow passing through the interior of the capsule by way of orifice constriction. That is to say, in the inhalant medicator made according to the invention defined in claim 3, the orifice plate, having a flow passage area less than the flow passage area of each of the holes pricked in the capsule, can adjust or control the flow velocity and the flow rate of the air flowing through the interior of the capsule.

According to the invention as claimed in claim 4, an orifice plate is located in at least one of the inflow and outflow passageways, and the flow-control orifice means of the inhalant medicator is constructed by a plurality of orifices having flow passage areas different from each other, and formed in the orifice plate in a manner so as to selectively communicate with the at least one of the inflow and outflow air passageways to optimally control the air flow passing through the interior of the capsule in accordance with a selectable orifice constriction. In the inhalant medicator made according to the invention defined in claim 4, depending upon switching between the plurality of orifices having different orifice-constriction characteristics, the flow velocity and the flow rate of the air flowing through the at least one of the inflow and outflow air passageways can be variably adjusted or controlled. That is, the best orifice size is selectable from the plurality of orifices, depending on physical properties of medicines enclosed in the capsule. This ensures stable dispersion of the medicines.

According to the invention as claimed in claims 5 and 6, the medicator body of the inhalant medicator is formed with an axial auxiliary air passage axially penetrating the medicator body in circumferentially spaced relationship with both the inflow passage and the outflow passage. Additionally, an auxiliary orifice is formed in the orifice plate as claimed in claims 3 and 4, for adjusting a flow passage area of the axial auxiliary air passage. As can be appreciated, the orifice plate is selectable from a plurality of orifice plates each of which is different from the other in auxiliary orifice size. In the inhalant medicator made according to the invention defined in claims 5 and 6, the best auxiliary orifice size is selectable depending on an adult of a large vital capacity, a child of a small vital capacity, a strong chest, or a weak chest. Thus, the auxiliary air quantity can be optimally adjusted or controlled by way of the auxiliary orifice formed in the orifice plate. The sole orifice plate may be formed with a plurality of auxiliary orifices spaced angularly circumferentially spaced from the previously-noted plurality of orifices and having flow passage areas different from each other, so as to selectively communicate with the axial auxiliary air passage formed in the medicator body. Thus, in the inhalant medicator equipped with the orifice plate having the plurality of auxiliary orifices of different auxiliary orifice sizes as well as the plurality of orifices of different orifice sizes, the flow velocity and the flow rate of the air flowing through the interior of the capsule can be variably adjusted or controlled and simultaneously the flow rate of auxiliary air is selectable depending on a vital capacity of a patient and a strong or weak breathing action of the patient.

DESCRIPTION OF THE PREFERRED EMBODIMENTS

The present invention will be hereinbelow described in detail in reference to the drawings (FIGS. 1 through 14) attached hereto.

Figure 1:
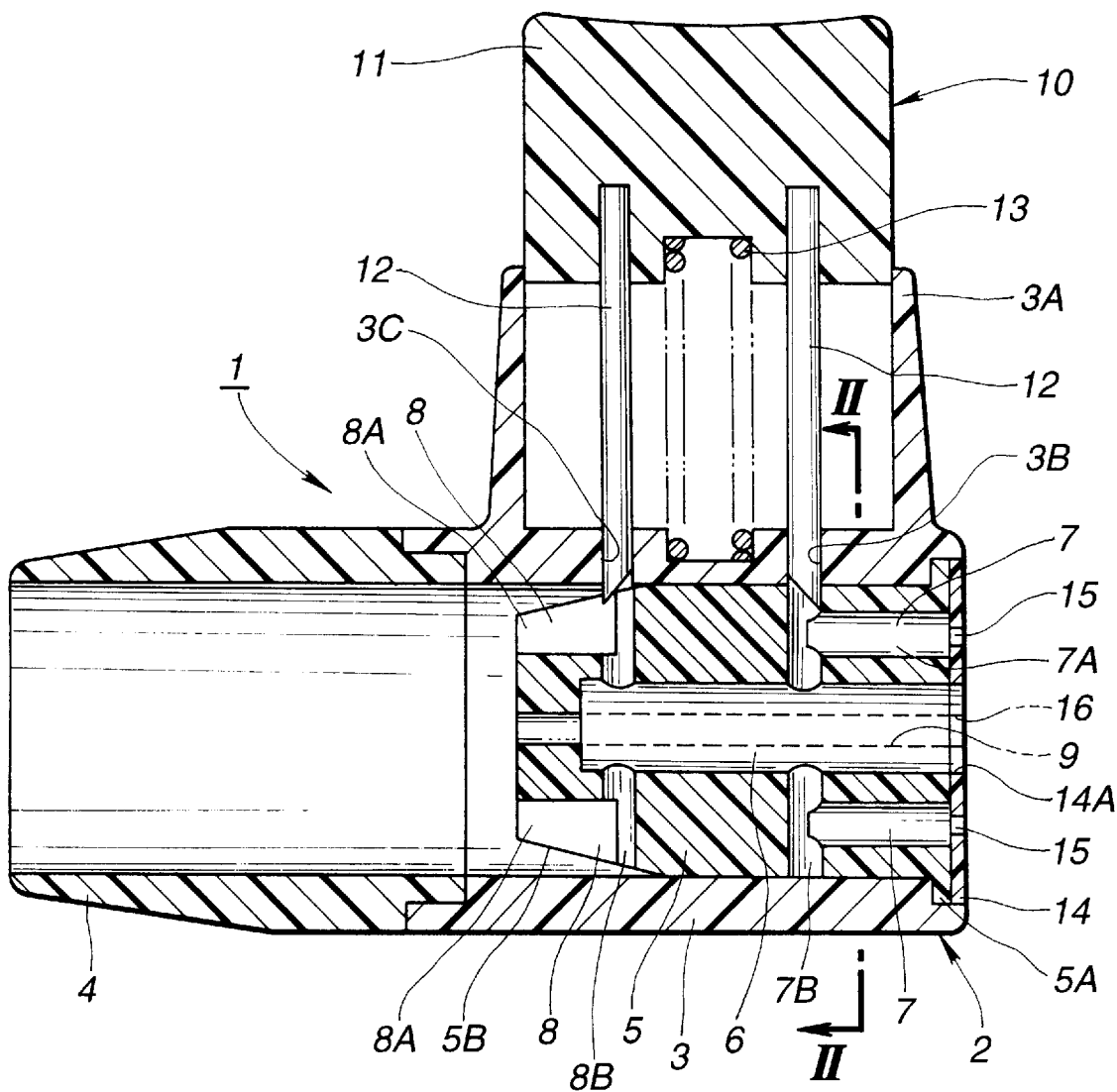
FIG. 1 is a cross-sectional view illustrating a first embodiment of an inhalant medicator.
Figure 2:
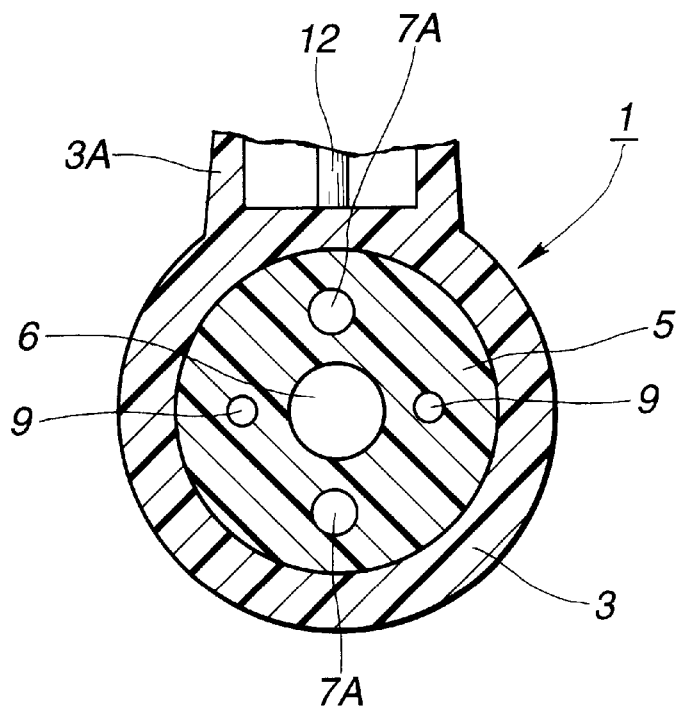
FIG. 2 is a lateral cross section of a holder accommodating portion and a capsule holder, taken along the line II—II of FIG. 1.
Figure 3:
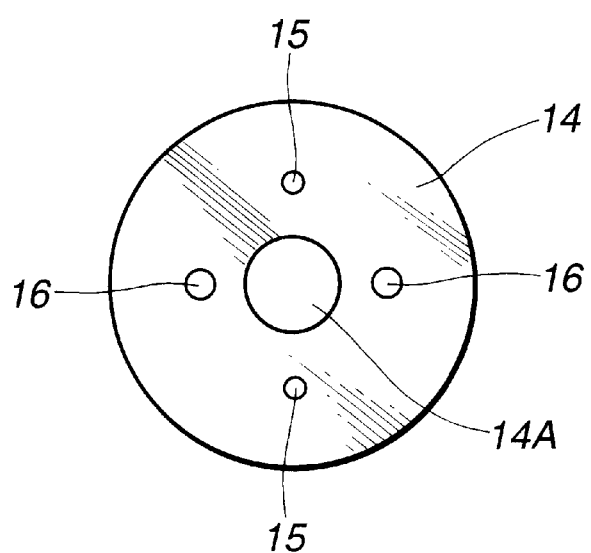
FIG. 3 is a plan view illustrating an orifice plate constructing part of the inhalant medicator of the first embodiment.
Figure 4:
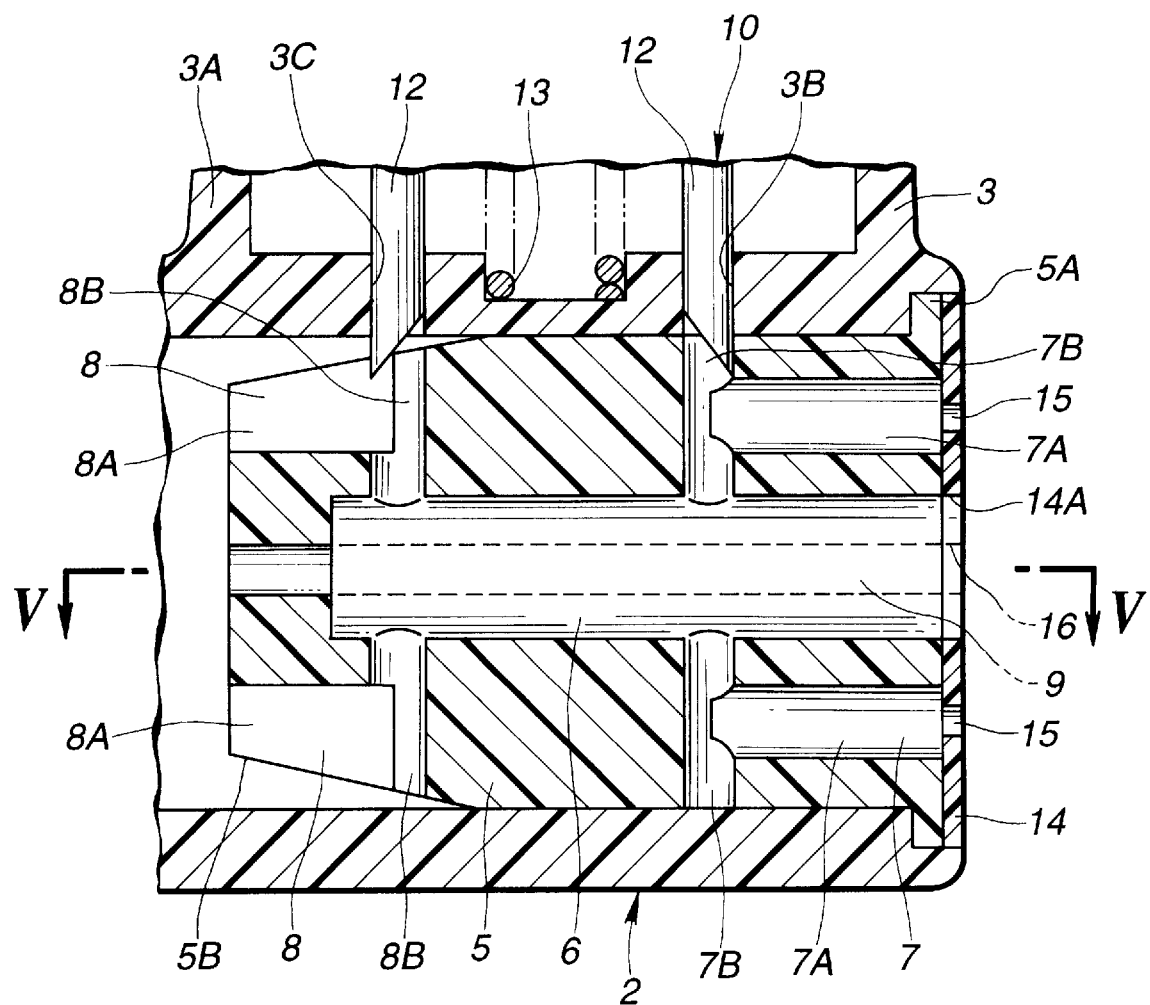
FIG. 4 is a partially enlarged cross section of an essential part including the holder accommodating portion, the capsule holder, and part of a boring tool employing pins.
Figure 5:
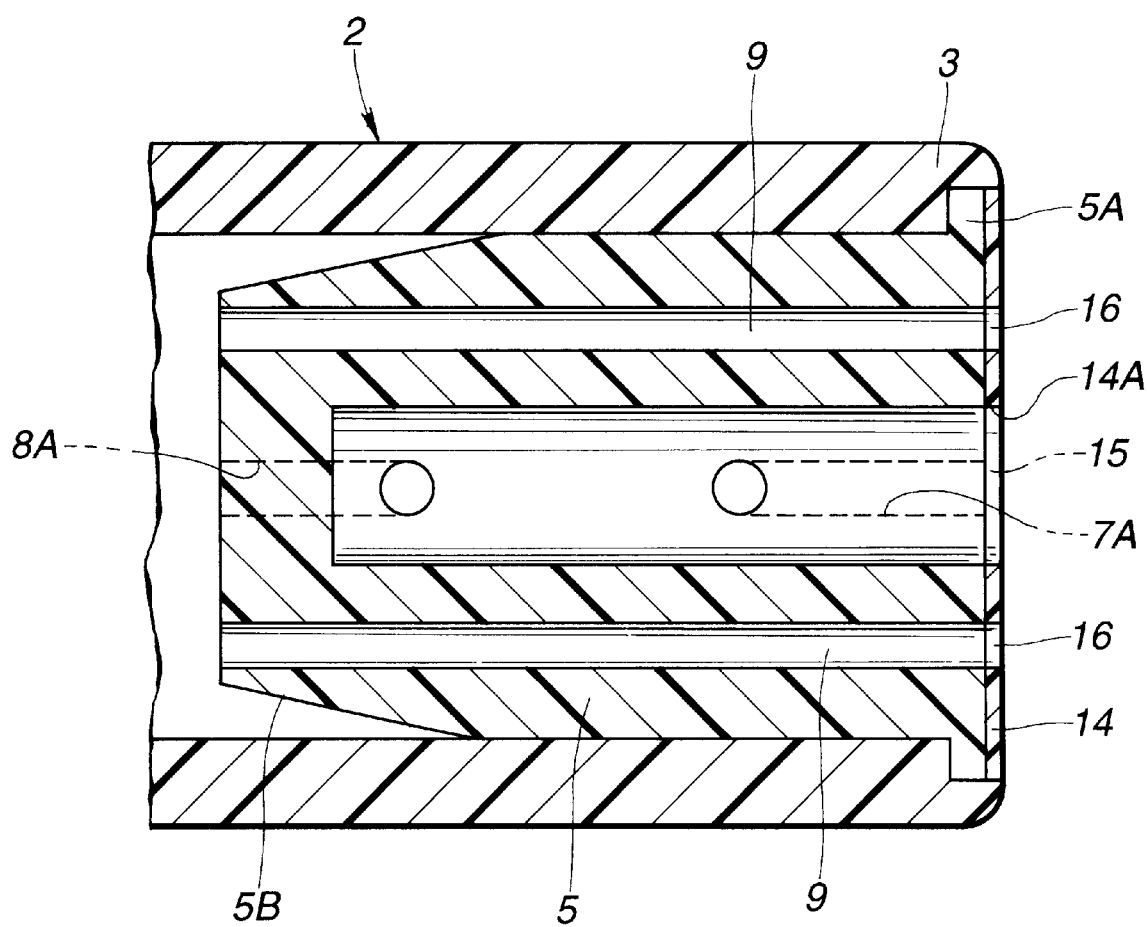
FIG. 5 is a lateral cross section of the holder accommodating portion and the capsule holder, taken along the line V—V of FIG. 4.
Figure 6:
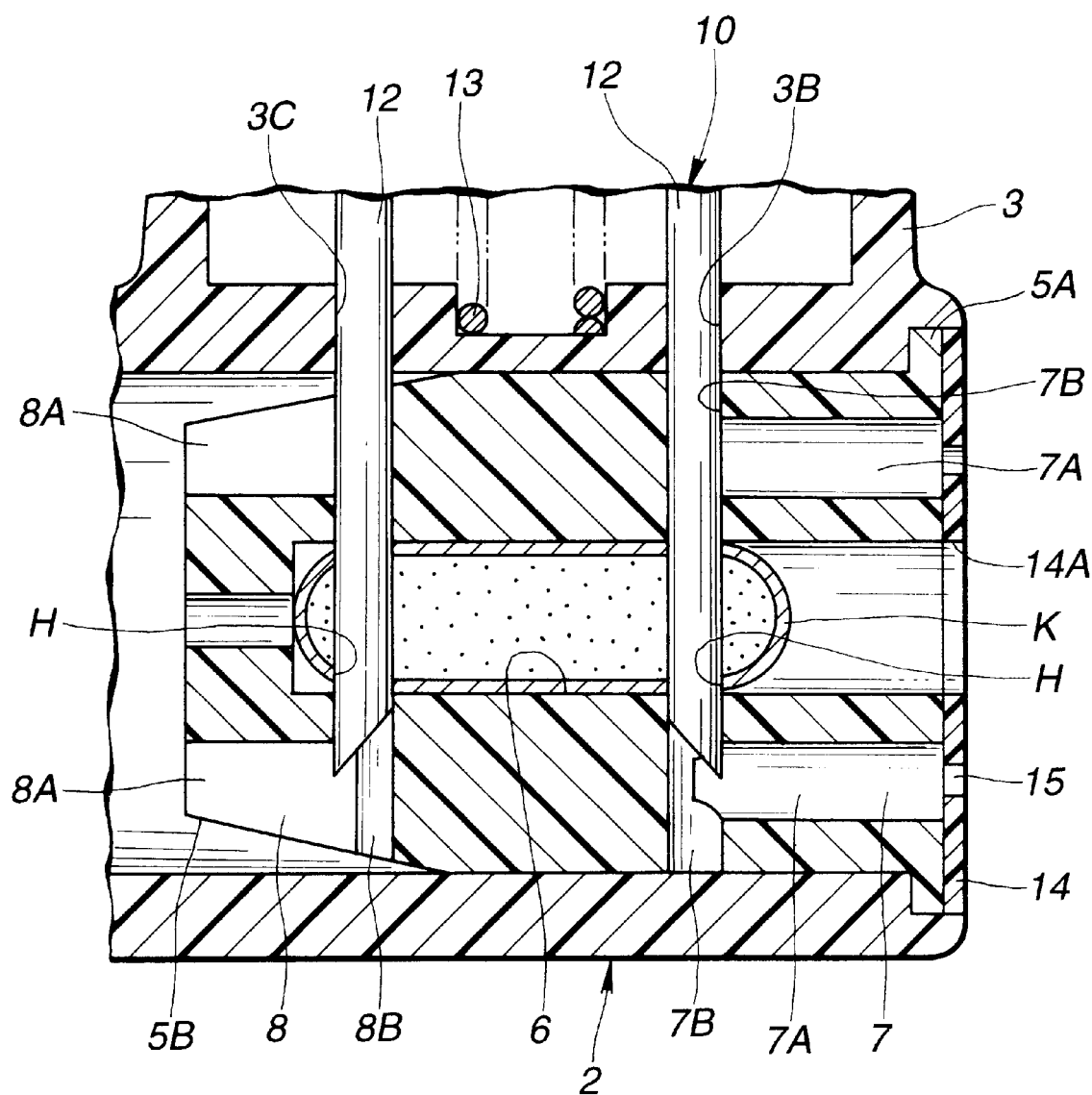
FIG. 6 is a partially enlarged cross section of the essential part of the inhalant medicator, in a particular state where holes are pricked in the capsule enclosed in the capsule holder and filled with granular medicines by means of the boring tool.

Referring now to FIGS. 1 through 7, there is shown the first embodiment of the inhalant medicator. Reference sign 1 denotes a medicator body. The medicator body 1 is comprised of an inhalant piece 2 and a capsule holder 5. The inhalant piece 2 is substantially cylindrical in shape. The inhalant piece 2 is mainly comprised of a holder accommodating portion 3 constructing one half of the inhalant piece for accommodating therein the capsule holder 5, and an inhalant port 4 constructing the other half of the inhalant piece and fitted to the holder accommodating portion 3. As seen in FIG. 1, the holder accommodating portion 3 is integrally formed with a cylindrical guide portion 3A on its outer periphery, so that the cylindrical guide portion 3A is projected radially outwardly from the outer periphery of the holder accommodating portion. As discussed later, the cylindrical guide portion 3A is provided to movably guide and support a pin support portion 11 of a boring tool 10. The holder accommodating portion 3 is formed with two radial bores 3B and 3C located within the cylindrical guide portion 3A and is in axially spaced relationship with each other. The Inhalant port 4 is detachably fitted to one axial end of the holder accommodating portion 3. The outer periphery of the other axial end of the holder accommodating portion 3 is gradually diametrically diminished in one axial direction of the inhalant piece. As seen in FIG. 5, the capsule holder 5 is fitted into the holder accommodating portion 3 and formed into a substantially cylindrical shape. The capsule holder 5 is integrally formed at its one axial end with a flanged portion 5A onto which the orifice plate 14 is fitted. The outer peripheral surface of the other axial end of the capsule holder 5 is formed with an outflow side tapered surface portion 5B gradually diametrically diminished in the axial direction of the capsule holder. Reference sign 6 denotes a center capsule housing area axially centrally extending in the capsule holder. One opening end (the right-hand opening end) of the capsule housing area 6 opens to the inflow side. As shown in FIG. 6, a capsule K is inserted into and accommodated in the capsule housing area 6 through the opening end. The capsule K is elliptically cylindrical in shape. The capsule is filled with very fine granular medicines. Reference signs 7, 7 denote two inflow air passageways formed in one axial end of the capsule holder 5. Each of the inflow air passageways 7, 7 are arranged around the capsule housing area 6. Each of the inflow air passageways 7, 7 comprises an axial inflow passage 7A arranged around the capsule housing area 6 and opening to the atmosphere through the opening end of the capsule holder 5, and a first radial pin insertion channel 7B communicating with the associated axial inflow passage 7A and extending radially in a manner so as to open to the capsule housing area 6. The respective pin insertion channel 7B communicates with the radial bore 3B of the holder accommodating portion 3. Each of the inflow air passageway 7 functions to communicate the capsule housing area 6 with the atmosphere. Reference signs 8, 8 denote two outflow air passageways formed in the other axial end of the capsule holder 5. Each of the outflow air passageways 8, 8 are arranged around the capsule housing area 6 to open to the inhalant port 4. Each of the outflow air passageways 8, 8 comprises an outflow passage 8A formed by cutting-out the outflow side tapered surface portion 5B of the capsule holder 5, and a second radial pin insertion channel 8B communicating with the associated outflow passage 8A and extending radially in a manner so as to open to the capsule housing area 6. The respective pin insertion channel 8B communicates with the radial bore 3C of the holder accommodating portion 3. Each of the outflow air passageway 8 functions to communicate the capsule housing area 6 with the inhalant port 4. Reference signs 9, 9 denote two auxiliary air passages arranged around the capsule housing area 6 and axially bored in the capsule holder 5. As shown in FIGS. 2 and 5, each of the auxiliary air passages 9, 9 is formed in such a manner as to extend in the axial direction at an angular position rotated by 90 degrees with respect to the respective axial inflow passage 7A. Each of the auxiliary air passages 9, 9 is provided to increase an auxiliary air quantity flowing through the inhalant medicator into the lungs of the patient during breathing action, thus avoiding difficulty in breathing. Returning to FIG. 1, reference sign 10 denotes a boring tool used for pricking holes (through openings) H in the capsule K accommodated in the capsule housing area 6. The boring tool 10 comprises the pin support portion 11 movably supported within the cylindrical guide portion 3A, two pins 12, 12 fixedly connected at their bottom ends to the pin support portion 11 and located or fitted at their tips into the respective radial bores 3B and 3C of the holder accommodating portion 3, and a return spring 13 operably disposed between the pin support portion 11 and the holder accommodating portion 3. The return spring 13 normally biases the pin support portion 11 in a direction that the pins 12, 12 move apart from the capsule K, in order to return the pins 12, 12 to their initial positions after pricking the holes H in the capsule K. In order to making four holes (or four through openings) H in the capsule K, the pin support portion 11 of the boring tool 10 is first 10 pushed into the cylindrical guide portion 3A against the bias of the return spring 13, and thus the tips of the pins 12, 12 penetrate the capsule K accommodated in the capsule housing area 6. In this manner, the four holes H can be formed in the capsule K by way of one push of the pin support portion 11. Upon removal of the pushing force applied to the pin support portion 11, the pin support portion 11 and the pins 12, 12 are returned to their initial positions by way of the bias of the spring 13. Reference sign 14 denotes the orifice plate. The orifice plate 14 is fitted onto the opening ends of the inflow air passageways 7, 7, that is, the right-hand side wall (viewing FIG. 1) of the capsule holder 5. The orifice plate 14 is formed at its center portion with a capsule insertion hole (simply a capsule hole) 14A communicating with the capsule housing area 6. Reference signs 15, 15 denote orifices serving as a means. As seen In FIG. 3, the orifices 15, 15 are formed in upper and lower positions of the orifice plate 14. The orifice plate 14 is fitted onto the flanged end of the capsule holder 5 such that the orifices 15 and 15 communicate the respective axial inflow passages 7A and 7A and such that the two orifices 15, 15 are point-symmetrical with respect to the axis of the orifice plate. In the inhalant medicator of the first embodiment, note that the orifice diameter (or the orifice size) of each of the orifices 15 and 15 is properly dimensioned to be less than a flow passage area of each of the through holes H pricked In the capsule K, and to be less than a flow passage area of each of the outflow air passageways 8 and 8. Due to the properly dimensioned orifice size, the respective orifice 15 functions to effectively adjust or control both a flow velocity and a flow rate of the air flowing through the associated inflow air passageway 7, the interior of the capsule K, and the associated outflow air passageway 8. Reference signs 16, 16 denote auxiliary orifices axially bored in the orifice, plate 14. As shown in FIG. 3, each of the auxiliary orifices 16, 16 is formed at an angular position rotated by 90 degrees with respect to the respective orifice 15, and communicates with the auxiliary air passage 9.

Hereunder explained is the flow of air passing through the medicator body 1. When the patient draws his or her breath while taking the inhalant port 4, outside air flows into the axial inflow passages 7A, 7A of the inflow air passageways 7, 7 via the orifices 15, 15 of the orifice plate 14, and then flows via the pin insertion channels 7B, 7B into the capsule K. The incoming air agitates granular medicines stored in the capsule K, and thus mixed with the granular medicines. The air flows out of the capsule K together with the agitated granular medicines. By means of the outflow air passageways 8, 8, the mixture of the incoming air and the granular medicines is discharged or carried via the pin insertion channels 8B, 8B through the axial inflow passages 8A, 8A into the inhalant port 4.

Hereinbelow described in detail the preparatory operation of the inhalant medication through which the patient inhales the granular medicines, and the flow of air and granular medicines during inhalation.

As regards the preparatory operation of the inhalant medication, first of all, a capsule K is inserted into and accommodated in the capsule housing area 6 from the opening end of the capsule holder 5. With the capsule K enclosed in the capsule housing area 6, as seen in FIG. 6, when the pin support portion 11 of the boring tool 10 is pushed into the cylindrical guide portion 3A along the inner peripheral wall of the guide portion 3A, the pins 12, 12 are radially inwardly inserted along the respective pin insertion channels 7B and 8B, thus pricking four through holes H in the capsule K with the pins 12, 12. After the formation of the four through holes H in the capsule K, the pin support portion 11 and the pins 12, 12 can be returned to their initial positions by means of the return spring 13.

Figure 7:
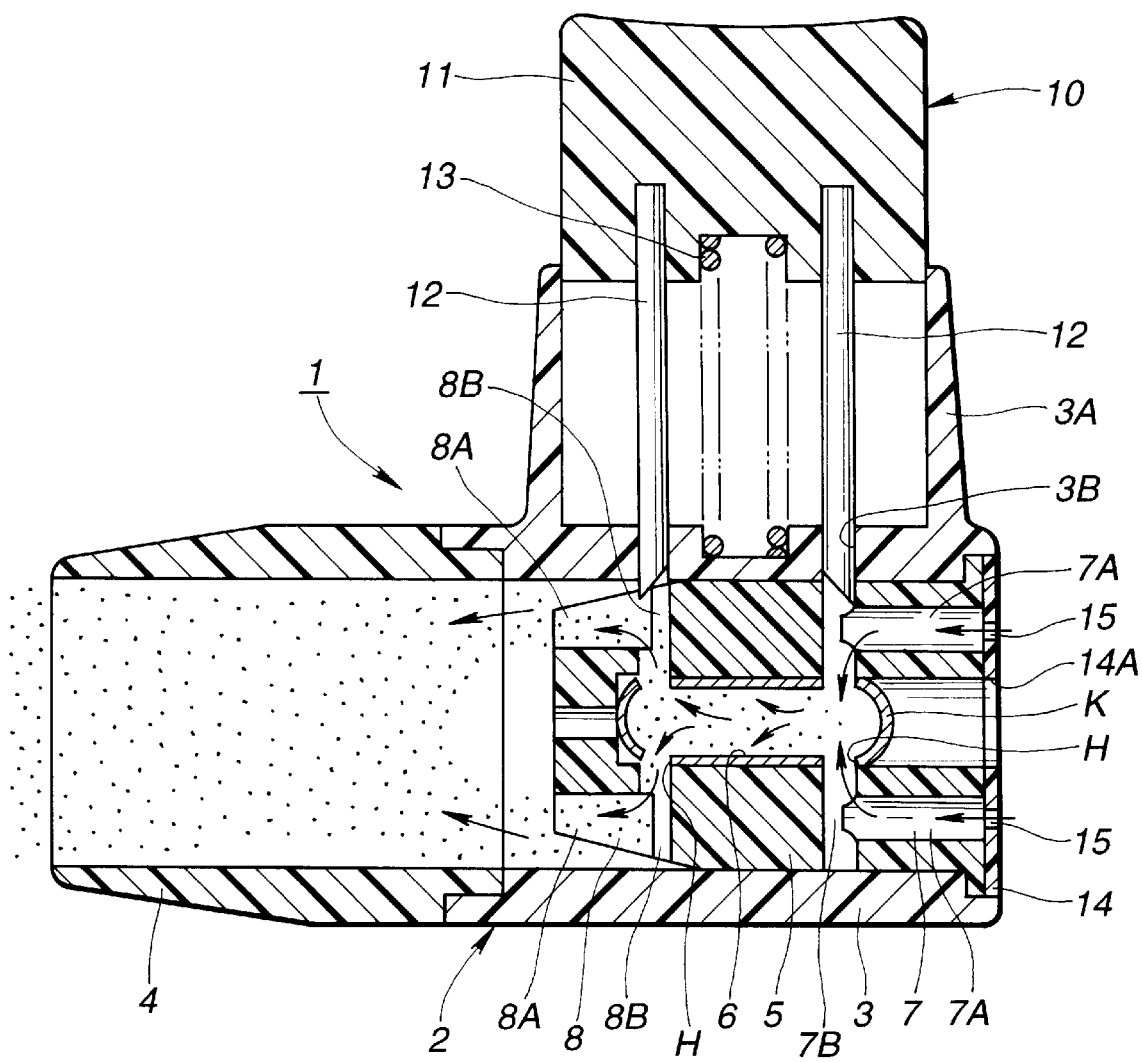
FIG. 7 is a cross section of the inhalant medicator of the first embodiment in a particular state where the granular medicines enclosed in the capsule are inhaled by the patient.

Hereunder discussed by reference to FIG. 7 is the detailed flow of air and granular medicines carried through the internal space or the internal flow passages of the inhalant medicator when the patient inhales the granular medicines. The patient draws his or her breath while taking the tapered end of the inhalant port 4, and whereby the air flows from the axial inflow passages 7A, 7A through the pin insertion channels 7B, 7B toward the capsule housing area 6, and then flows via the right-hand through holes H, H as indicated by the arrow of FIG. 7. Thus, the air introduced into and passing through the interior of the capsule K functions to forcibly agitate and diffuse the granular medicines enclosed in the capsule K, and as a result the introduced air is effectively blended with the granular medicines. Thereafter, the air containing the granular medicines enclosed in the capsule K, that is, the mixture of air and granular medicines, can be discharged through the left-hand through holes H, H via the outflow side pin insertion channels 8B, 8B and the outflow passages 8A, 8A into the inhalant port 4. In this manner, the mixture of air and granular medicines can be effectively inhaled from the inhalant port 4 through the oral cavity and the trachea of the patient into the lungs. As explained above, the granular medicines can be prescribed toward within the lungs of the patient. As can be appreciated from the above, in the inhalant medicator of the first embodiment is equipped with an orifice 15 fitted onto the opening end of the axial inflow passage 7A of the inflow air passageway 7 and having a flow passage area less than a flow passage area of the through hole H, and thus the flow velocity and the flow rate of air flowing through the inflow air passageway 7, the interior of the capsule K, and the outflow air passageway 8 can be both adjusted or controlled by the specified orifice size (i.e., the flow passage area) of the orifice 15.

Additionally, the flow passage area of the orifice 15 is dimensioned to be less than the flow passage area of the through hole H pricked in the capsule K, and thus the flow velocity and the flow rate of the air flowing through the interior of the capsule K can be controlled to predetermined values, irrespective of fluctuations in size of the through hole H pricked in the capsule K. This insures stable dispersion of the granular medicines. As a result of this, a patient can efficiently inhale granular medicines every medications, and whereby the reliability of the inhalant medicator can be enhanced. FIG. 3 shows the orifice plate 14 formed with the two diametrically-opposing orifices 15 and 15 whose orifice sizes are identical to each other. It will be easily appreciated that various orifice plates of different orifice sizes may be prepared, accounting for the difference of dispersion properties of various medicines. For example, in case of granular medicines of a strong condensation property (bad dispersion), it is preferable to select an orifice plate having an orifice of a comparatively small orifice diameter from various sorts of orifice plates. Conversely, in case of granular medicines of a weak condensation property (good dispersion), it is preferable to select an orifice plate having an orifice of a comparatively large orifice diameter. As set forth above, various kinds of granular medicines having physical properties different from each other can be efficiently prescribed by properly selecting one of a plurality of orifice plates having different orifice sizes. In the same manner discussed above, various kinds of orifice plates of different auxiliary orifice sizes may be prepared, accounting for the difference of vital capacity between a child and an adult. For example, in case of a child of a relatively small vital capacity, it is preferable to select an orifice plate having an auxiliary orifice of a comparatively large orifice diameter. Conversely, in case of an adult of a relatively large vital capacity, it is preferable to select an orifice plate having an auxiliary orifice of a comparatively small orifice diameter. In this case, it is possible to ensure the air flow rate suitable for a vital capacity (or a breathing action) of a patient by adjusting the flow rate of auxiliary air flowing through the auxiliary air passage 9 by means of the auxiliary orifice properly selected.

The second embodiment is hereunder described in detail by reference to FIG. 8. The inhalant medicator of the second embodiment is characterized in that an outflow air passageway 24 is constructed as a flow-constriction passageway having a flow passage area less than the flow passage area of the through hole H pricked in the capsule K. The same reference signs used to designate elements in the first embodiment shown in FIGS. 1 through 7 will be applied to the corresponding elements used in the second embodiment shown in FIG. 8, for the purpose of comparison of the first and second embodiments. Detailed description of the same reference signs will be omitted because the above description thereon seems to be self-explanatory. Reference sign 21 denotes a capsule holder used for the inhalant medicator of the second embodiment, in place of the capsule holder employed in the inhalant medicator of the first embodiment. The capsule holder 21 is formed at its one axial end integral with a flanged portion 21A. The capsule holder 21 is also formed with an axial capsule housing area 22 extending along the central axis of the capsule holder. The right-hand half of the capsule holder 21 is formed with inflow air passageways 23 and 23, each comprising an axial inflow passage 23A arranged around the capsule housing area 22 and a radial pin insertion channel 23B, whereas the left-hand half of the capsule holder 21 is formed with outflow air passageways 24 and 24, each comprising an axial outflow passage 24A arranged around the capsule housing area 22 and a radial pin insertion channel 24B. In the second embodiment, note that the axial outflow passage 24A constructing part of the outflow air passageway 24 is formed as a flow-constriction passageway having a flow passage area less than the through hole H pricked in the capsule K. Additionally, the capsule holder 21 is formed with axial auxiliary air passages 25, each axially penetrating the capsule holder 21 of the medicator body 2 in circumferentially spaced relationship with both the inflow and outflow passages 23A and 24A. As discussed above, in the second embodiment, part of the outflow air passageway is formed as a flow-constriction passageway, and therefore the flow velocity and the flow rate of air flowing through the interior of the capsule K can be controlled by flow-constricting action of the flowconstriction passageway. Thus, the inhalant medicator of the second embodiment using the capsule holder 21 can provide the same effects as the first embodiment.

Figure 9:
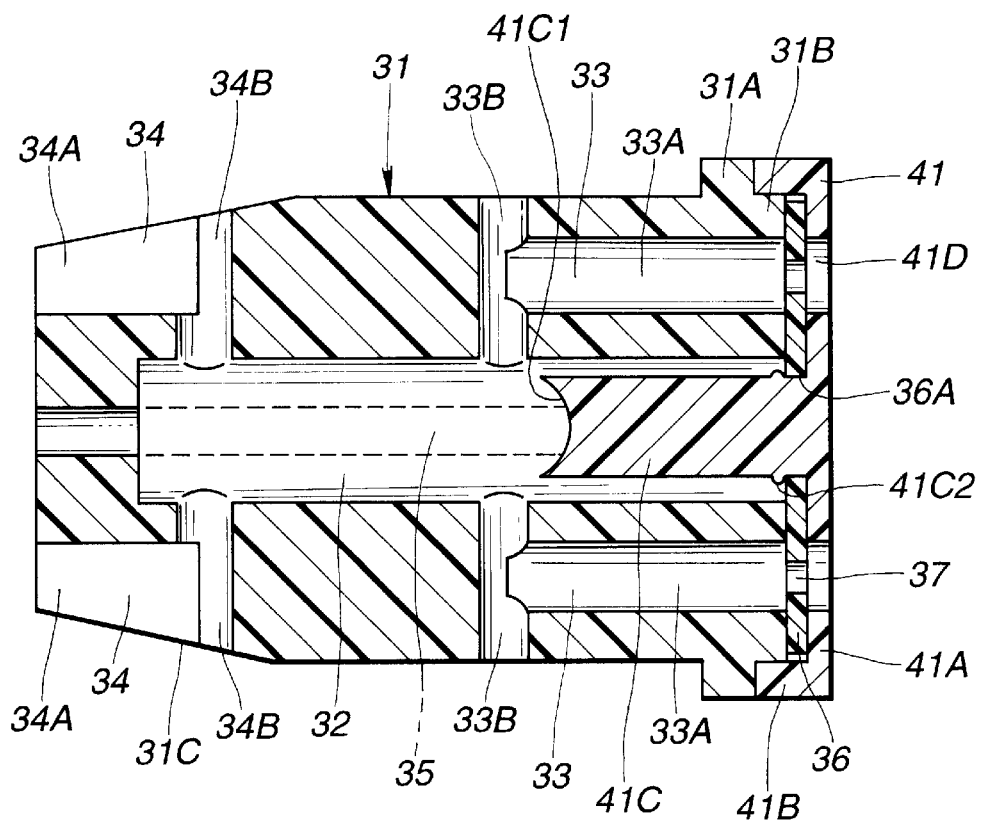
FIG. 9 is a longitudinal cross section of a capsule holder employed in an inhalant medicator of a third embodiment.
Figure 10:
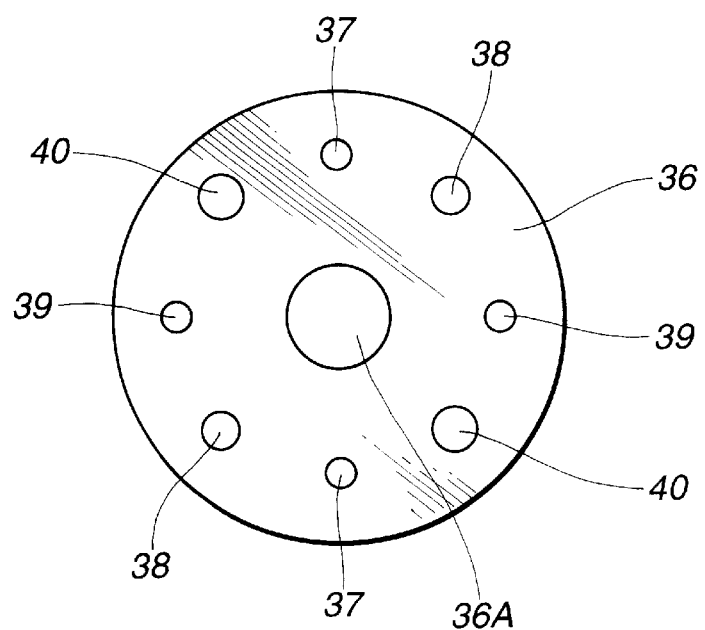
FIG. 10 is a plan view illustrating an orifice plate employed in the inhalant medicator of the third embodiment.
Figure 11:
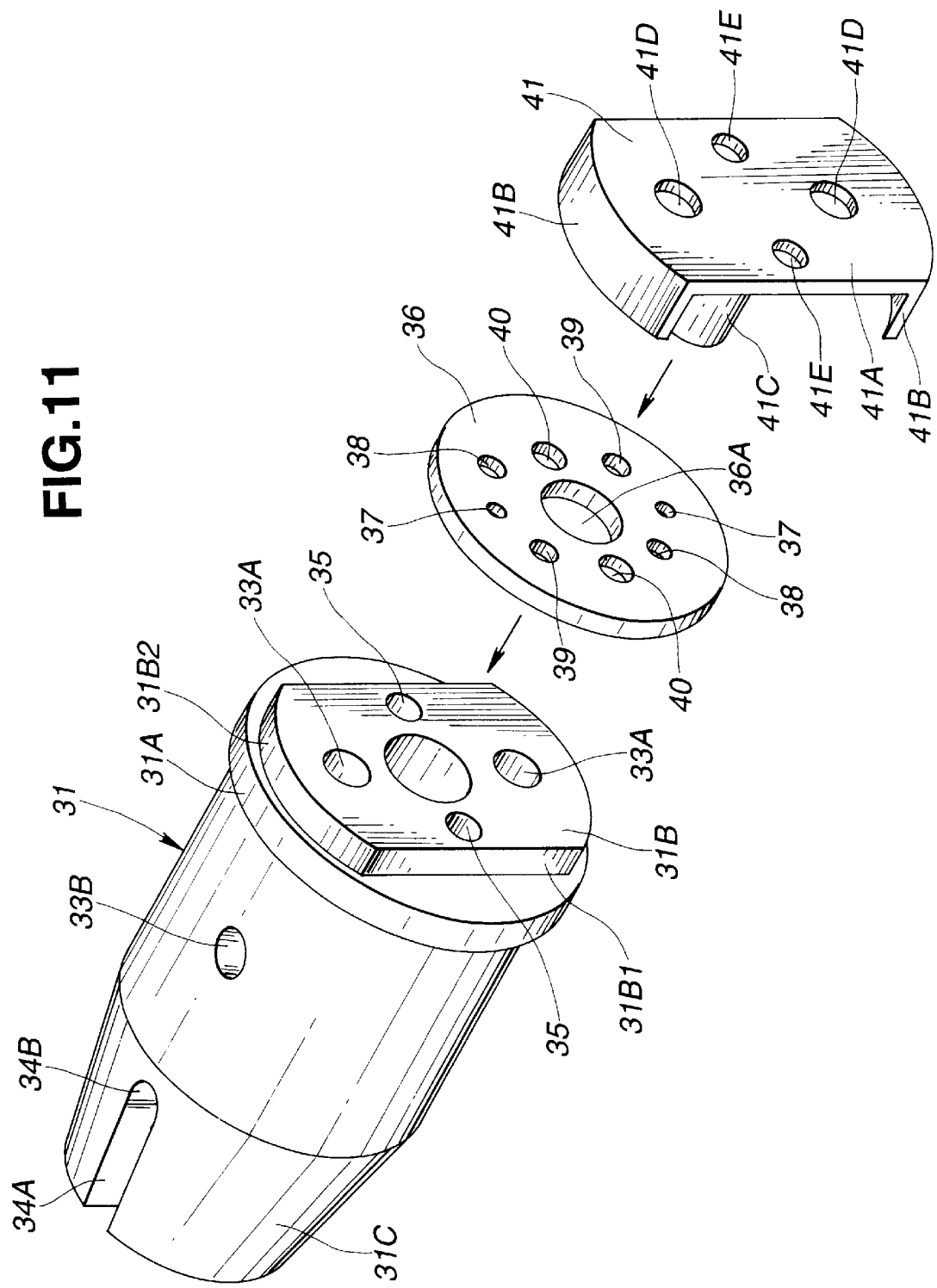
FIG. 11 is a disassembled view of the capsule holder used for the inhalant medicator of the third embodiment.
Figure 12:
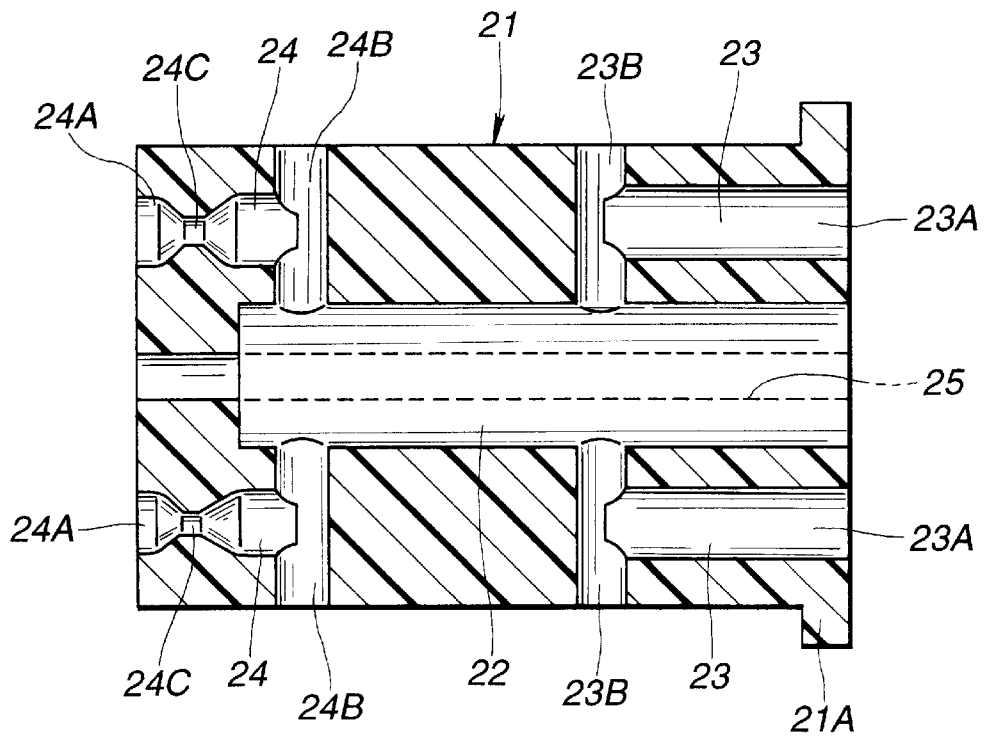
FIG. 12 is a longitudinal cross section of a first modification of a capsule holder having a flow-constriction portion formed in each of the outflow passages included in the outflow air passageway, cut in the same cutting surface as FIG. 8.
Figure 13:
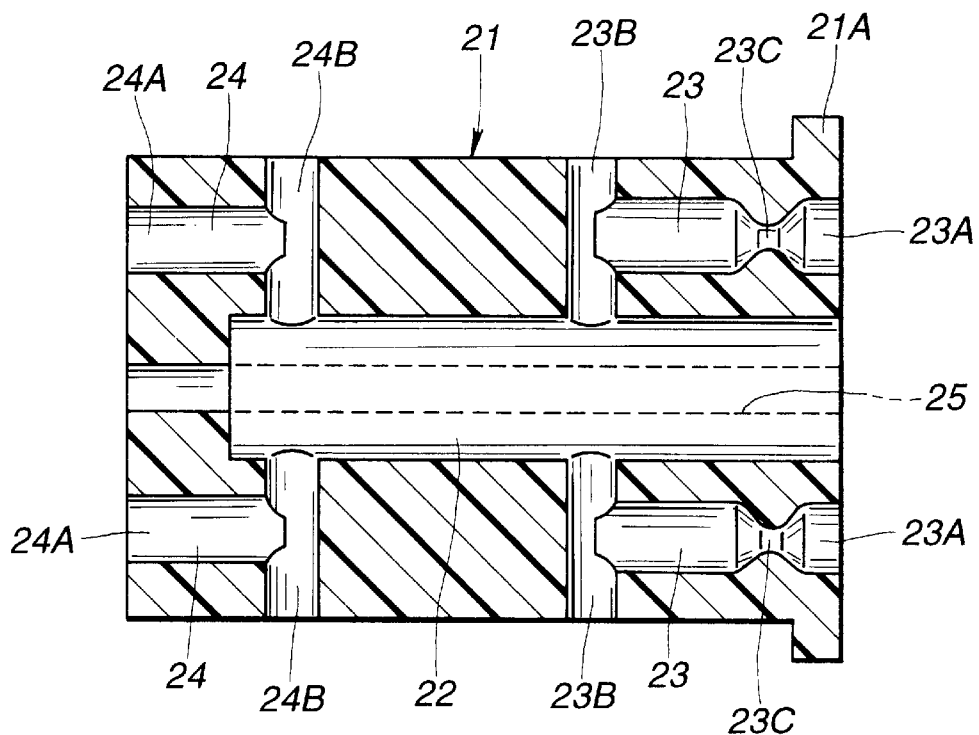
FIG. 13 is a longitudinal cross section of a second modification of a capsule holder having a flow-constriction portion formed in each of the axial inflow passages included in the inflow air passageway, cut in the same cutting surface as FIG. 8.

The third embodiment is hereunder described in detail by reference to FIGS. 9 through 11. The inhalant medicator of the third embodiment is characterized in that an orifice plate is located in and fitted to the opening end of the inflow air passageway, and a flow-control orifice means comprises a plurality of orifices having flow passage areas different from each other, and formed in the orifice plate in a manner so as to selectively communicate with the inflow air passageway. The same reference signs used to designate elements in the first embodiment shown in FIGS. 1 through 7 will be applied to the corresponding elements used in the third embodiment shown in FIGS. 9, 11, for the purpose of comparison of the first and third embodiments, and detailed description of the same reference signs will be omitted. Reference sign 31 denotes a capsule holder used for the inhalant medicator of the third embodiment, in place of the capsule holder 5 of the first embodiment. The capsule holder 31 is formed almost in the same manner as the capsule holder 5. The capsule holder 31 is formed at its one axial end integral with a flanged portion 31A. The capsule holder 31 is further formed with a stepped portion 31B axially projecting from the flanged portion 31A. The stepped portion 31B has two parallel, diametrically-opposing flat faced portions 31B1, 3113 and two diametrically-opposing circular-arc portions (upper and lower circular-arc portions) 31B2, 31B2. For example, the flat faced portions 31B1 and 31B1 are formed by cutting out left and right circular-arc portions. The outer peripheral surface of the other axial end (the left-hand axial end) of the capsule holder 31 is formed with an outflow side tapered surface portion 31C gradually diametrically diminished in the axial direction of the capsule holder 31. The right-hand half of the capsule holder 31 is formed with inflow air passageways 33 and 33, each comprising an axial inflow passage 33A arranged around the capsule housing holder 32 and a radial pin insertion channel 33B, whereas the left-hand half of the capsule holder 31 is formed with outflow air passageways 34 and 34, each comprising an outflow passage 34A arranged around the capsule housing area 32 and a radial pin insertion channel 34B. Actually, as seen from the perspective view shown in FIG. 11, the two axial inflow passages 33A and 33A are located above and below the capsule housing area 32. Similarly, the two outflow passages 34A and 34A are located above and below the bottom end of the capsule housing area 32. The capsule holder 31 is also formed in the left and right of the capsule housing area 32 with two auxiliary air passages 35 and 35. Reference sign 36 denotes a disc-like orifice plate. The disc-like orifice plate 36 is fitted onto the opening ends of the inflow air passageways 33 and 33, that is, the right-hand side wall (viewing FIG. 9) of the capsule holder 31. As shown in FIG. 10, the orifice plate 36 is formed at its center portion with a support hole 36A through which a support shaft 41C of a support plug 41 is partly inserted into the capsule housing hole 32. As seen in FIG. 10, two diametrically-opposing small-diameter orifices 37 and 37 are formed in the orifice plate 36 above and below the support hole 36A. Two diametrically-opposing large-diameter orifices 38 and 38 are formed in the orifice plate 36 at angular positions rotated clockwise (viewing FIG. 10) by 45 degrees from the respective small-diameter orifices 37, 37. As may be appreciated, either the small-diameter orifice 37 or the large-diameter orifice 38 can be communicated with the associated axial inflow passage 33A by rotating the orifice plate 36 about the support shaft 41C.

As clearly seen in FIG. 10, the orifice plate 36, fitted to the capsule holder 31 of the third embodiment, is also formed with two diametrically-opposing small-diameter auxiliary orifices 39 and 39, located at angular positions rotated by 90 degrees from the respective small-diameter orifices 37 and 37. Additionally, the orifice plate 36 is formed with two diametrically-opposing large-diameter auxiliary orifices 40 and 40, located at angular positions rotated by 90 degrees from the respective large-diameter orifices 38 and 38. As can be appreciated from FIGS. 9 and 10, either the small-diameter auxiliary orifice 39 or the large-diameter auxiliary orifice 40 can be communicated with the associated axially-extending auxiliary air passage 35 by rotating the orifice plate 36 about the support shaft 41C. In case of the use of the orifice plate 36 shown in FIG. 10, a combination between the small-diameter orifice 37 and the small-diameter auxiliary orifice 39 ensures a full fluid communication between the orifice 37 and the axial inflow passage 33A and a full fluid communication between the small-diameter auxiliary orifice 39 and the auxiliary air passage 35 at a certain phase angle of the orifice plate 36 as shown in FIG. 10. The combination of the orifices 37 and 39 is suitable for a particular condition where a granular medicine of a bad dispersion is combined with a patient of a large vital capacity. A combination between the large-diameter orifice 38 and the large-diameter auxiliary orifice 40 ensures a full fluid communication between the orifice 38 and the axial inflow passage 33A and a full fluid communication between the large-diameter auxiliary orifice 40 and the auxiliary air passage 35 at a phase angle of the orifice plate 36 rotated by 90 degrees from the angular position shown in FIG. 10. The combination of the orifices 38 and 40 is suitable for a particular condition where a granular medicine of a good dispersion is combined with a patient of a small vital capacity. Alternatively, as clearly seen in FIG. 11, the orifice plate 36, fitted to the capsule holder 31 of the third embodiment, is also formed with two diametrically-opposing small-diameter auxiliary orifices 39 and 39, located at angular positions rotated by 90 degrees from the respective large-diameter orifices 38 and 38. Additionally, the orifice plate 36 is formed with two diametrically-opposing large-diameter auxiliary orifices 40 and 40, located at angular positions rotated by 90 degrees from the respective small-diameter orifices 37 and 37. In case of the use of the orifice plate shown in FIG. 11, different from the orifice plate shown in FIG. 10, in relative-position relationship between the small-diameter orifice 37 and the auxiliary small-diameter orifice 39 and in relative-position relationship between the large-diameter orifice 38 and the large-diameter auxiliary orifice 40, a combination between the small-diameter orifice 37 and the large-diameter auxiliary orifice 40 ensures a full fluid communication between the orifice 37 and the axial inflow passage 33A and a full fluid communication between the large-diameter auxiliary orifice 40 and the auxiliary air passage 35 at a certain phase angle of the orifice plate 36 as shown in FIG. 11.

The combination of the orifices 37 and 40 is suitable for a particular condition where a granular medicine of a bad dispersion is combined with a patient of a small vital capacity. On the other hand, a combination between the large-diameter orifice 38 and the small-diameter auxiliary orifice 39 ensures a full fluid communication between the orifice 38 and the axial inflow passage 33A and a full fluid communication between the small-diameter auxiliary orifice 39 and the auxiliary air passage 35 at a phase angle of the orifice plate 36 rotated by 90 degrees from the angular position shown in FIG. 11. The combination of the orifices 38 and 39 is suitable for a particular condition where a granular medicine of a good dispersion is combined with a patient of a large vital capacity. As discussed above, the small-diameter orifices 37, 37 and the large-diameter orifices 38, 38 serve as the flow-control orifice means. The flow passage area of each of the small-diameter orifices 37, 37 and the flow passage area of each of the large-diameter orifices 38, 38 are both dimensioned to be less than the flow passage area of the through hole H pierced or pricked in the capsule K. Thus, the flow velocity and the flow rate of air flowing through the interior of the capsule K can be properly controlled or adjusted by means of the orifices 37 or 38. In addition, the quantity of auxiliary air flowing through the respective auxiliary air passage 35 is determined by the orifice size of the auxiliary orifice (39, 40). In other words, the quantity of auxiliary air flowing through the auxiliary air passage 35 can be effectively adjusted or controlled by means of the auxiliary orifices 37 or 38. In FIGS. 9 and 11, reference sign 41 denotes the support plug insertable into the right-hand end of the capsule holder 31, for rotatably supporting the orifice plate 36 at the stepped portion 31B of the capsule holder 31. As seen in FIG. 11, the support plug 41 comprises a lid portion 41A having left and right cut-out portions formed by cutting out circular-arc portions, upper and lower axially-extending circular-arc support pieces 41B and 41B formed integral with the lid portion 41A, the support shaft 41C axially extending from the center of the lid portion 41A and integrally connected to the center of the inside of the lid portion 41A, upper and lower air inlet holes 41D and 41D formed or bored in the lid portion 41A above and below the central support shaft 41C and having approximately the same inside diameter as the axial inflow passage 33A being circular in lateral cross-section, and auxiliary orifices 41E and 41E located at angular positions rotated by 90 degrees from the respective air inlet holes 41D and 41D and bored in the lid portion 41A in such a manner as to have approximately the same inside diameter as the axially-extending auxiliary air passage 35. As best seen in FIG. 9, the innermost end surface of the support shaft 41C is formed as a capsule-end pushing concave portion 41C1. As shown in FIG. 9, an annular ridged portion 41C2 is formed on the outer periphery of the support shaft 41C near the joint between the root of the support shaft 41C and the center of the lid portion 41A. The relationship of installation among the capsule holder 31, the orifice plate 36, and the support plug 41 is described hereunder.

In mounting the orifice plate 36 on inner wall surface of the support plug 41, the support shaft 41C is inserted into the support hole 36A until one side wall of the orifice plate 36 is fitted onto the inner wall surface of the lid portion 41A, and as a result the orifice plate 36 is sandwiched between the annular, slightly ridged portion 41C2 formed on the root of the support shaft 41C and the inside wall surface of the lid portion 41A, so that the orifice plate 36 can be rotatably supported relative to the support plug 41 between the slightly ridged portion 41C2 and the lid inside wall.

In other words, the annular ridged portion 41C2 provides a proper snapping action of the orifice plate 36 on the support plug 41, while permitting rotational motion of the orifice plate 36 on the support shaft 41C.

Figure 8:
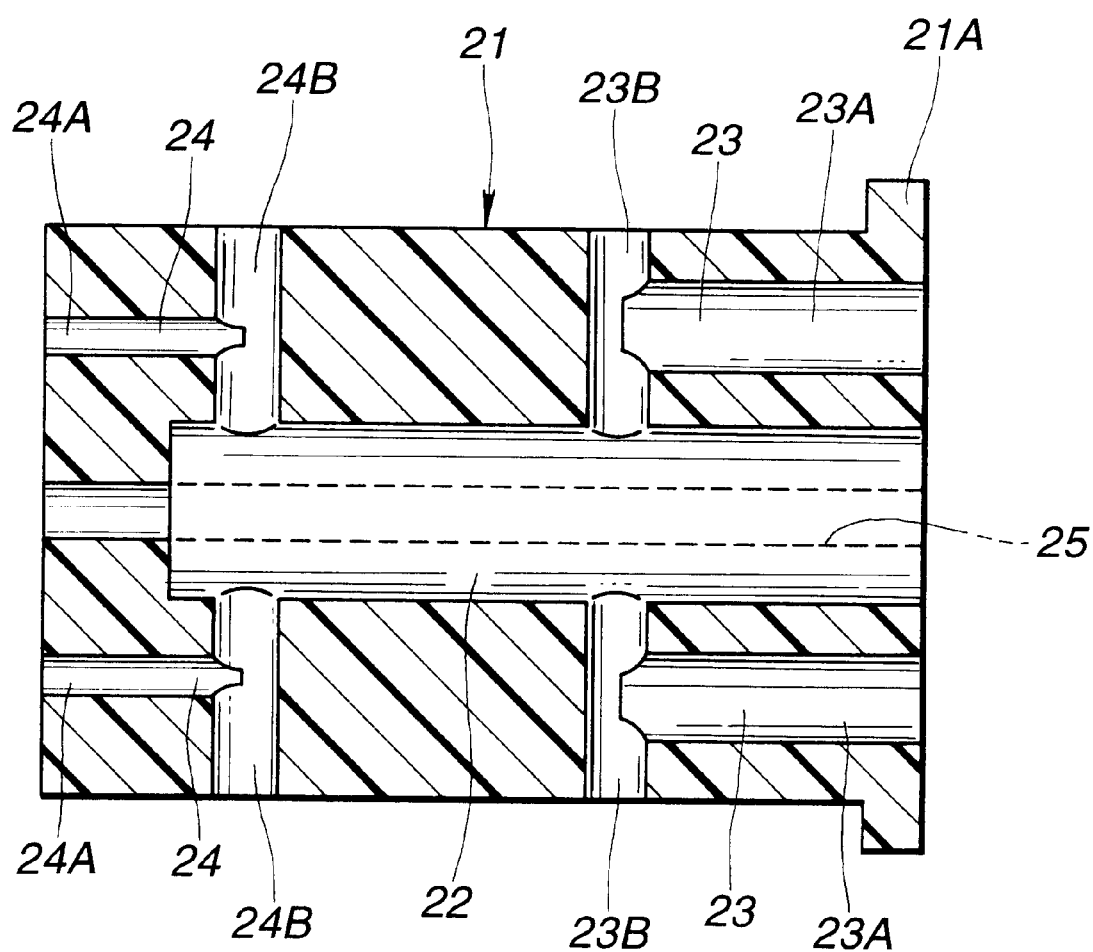
FIG. 8 is a longitudinal cross section of a capsule holder employed in an inhalant medicator of a second embodiment.

Thereafter, the support plug 41 integrally connected to the orifice plate 36, snapped back to the unstressed place (the space between the annular ridged portion 41C2 and the inside wall surface of the lid portion 41A), is fitted to the stepped portion 31B the capsule holder 31, such that the support shaft 41C is inserted into the capsule housing area 32, and then the upper and lower axially extending support pieces 41b and 41b are somewhat tightly but detachably fitted onto the upper and lower circular-arc portions 31B2 and 31B2 of the stepped portion 31B. Therefore, under a condition where the three members 36, 41, and 31 are assembled with each other, the outer periphery of the orifice plate 36 is partly projected from each of the two parallel flat-faced portions 31B1 and 31B1. The orifice plate 36 can be properly rotated relative to the capsule holder 31 by rotating the previously-noted partly projected portions of the orifice plate 36 by the patient's fingers. As discussed above, in the inhalant medicator of the third embodiment, the orifice plate 36 having the small-diameter orifices 37 and 37 and the large-diameter orifices 38 and 38 is rotatably mounted on the stepped end of the capsule holder 31. Therefore, when granular medicines of a bad dispersion are prescribed for a patient, it is possible to increase the flow velocity of air flowing through the interior of the capsule K and to efficiently diffuse the granular medicines, thus enhancing the property of dispersion of the medicines, by selecting the small-diameter orifices (37, 37) from the different orifices 37 and 38. To the contrary, when granular medicines of a good dispersion are prescribed for a patient, it Is possible to suitably decrease the flow velocity of air flowing through the interior of the capsule K by selecting the large-diameter orifices (38, 38) from the different orifices 37 and 38. In this manner, various granular medicines can be optimally dispersed by suitably selecting either the small-diameter orifice 37 or the large-diameter orifice 38, depending on physical properties of the granular medicines. The previously-described selection of the orifice size from the small-diameter orifice 37 and the large-diameter orifice 38 ensures proper adjustment of both the flow velocity and the flow rate of air flowing through the interior of the capsule, irrespective of good or bad properties of dispersion of medicines. This enables optimal dispersion of the medicines carried from the capsule into the inhalant port 4, and whereby the patient can efficiently inhale the medicines within toward their lungs. In the inhalant medicator of the third embodiment, in addition to the small-diameter orifices 37 and 37 and the large-diameter orifices 38 and 38, the disc-like orifice plate 36 has the small-diameter auxiliary orifices 39 and 39 and the large-diameter auxiliary orifices 40 and 40 axially bored in the orifice plate 36. The quantity of auxiliary air flowing through the auxiliary air passage 35 can be easily adjusted by suitably selecting either the small-diameter auxiliary orifice 39 or the large-diameter auxiliary orifice 40, depending on the vital capacity of the patient (or a strong or weak breathing action of the patient). That is, the inhalant medicator of the third embodiment can provide a proper quantity of auxiliary air flowing through the medicator body, depending on a child (a relatively small vital capacity) or an adult (a relatively large vital capacity).

Referring now to FIG. 12, there is shown a first modification of the capsule holder 21 employed in the inhalant medicator of the second embodiment shown in FIG. 8. As previously described, in the second embodiment, although the axial outflow passage 24A of the outflow air passageway 24 is formed as a flow-constriction passageway having a comparatively small flow passage area less than the through hole H pierced in the capsule, the axial outflow passage 24A may be formed with a partial flow-constriction portion 24C (see the left-hand side cross section of FIG. 12) in place of the flow-constriction passageway having the same lateral cross section in the axial direction. Alternatively, as can be appreciated from a second modification (see FIG. 13) of the capsule holder 21 employed in the inhalant medicator of the second embodiment shown in FIG. 8, the axial inflow passage 23A may be formed with a partial flow-constriction portion 23C (see the right-hand side cross section of FIG. 13) in place of the flow-constriction passageway 24A of the second embodiment. As discussed above, according to the first modification (see FIG. 12) of the capsule holder, the axial outflow passage 24A is partly constricted in the middle thereof. According to the second modification (see FIG. 13) of the capsule holder, the axial inflow passage 23A is partly constricted in the middle thereof. Thus, the first (FIG. 12) and second (FIG. 13) modifications can provide the same effects as the capsule holder of the second embodiment (FIG. 8).

Figure 14:
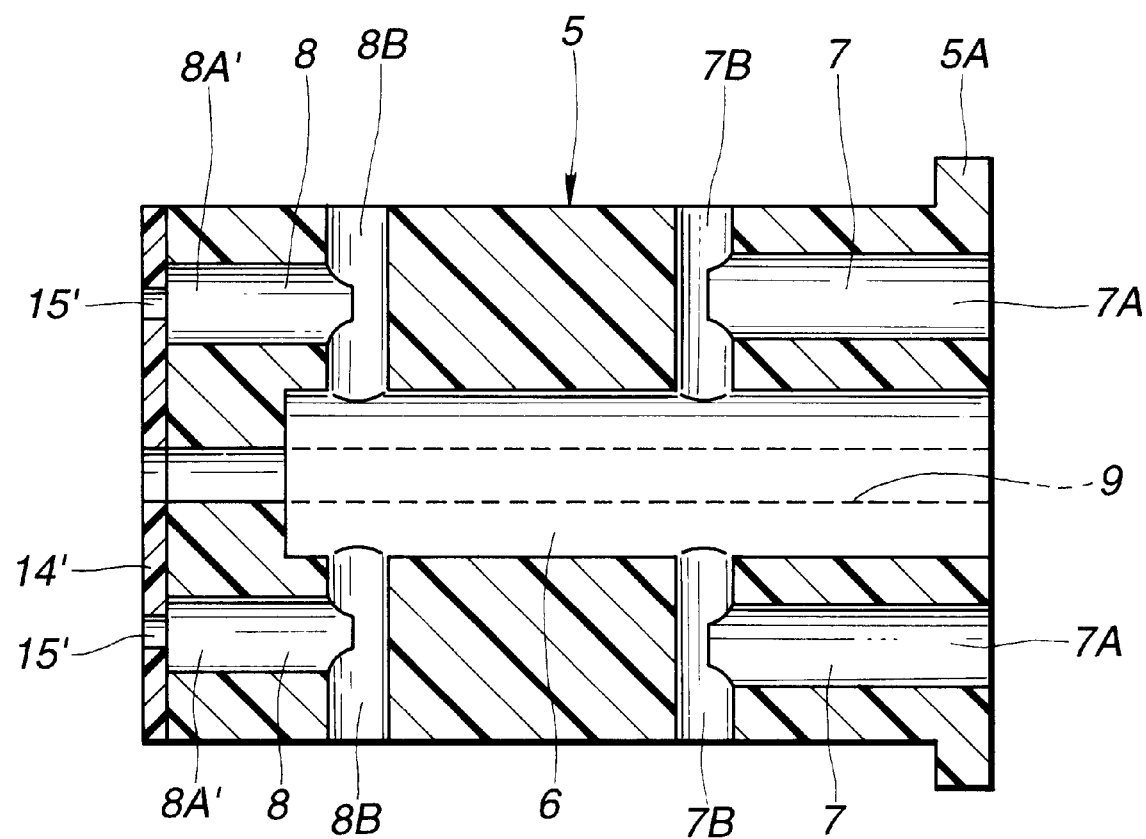
FIG. 14 is a longitudinal cross section of a third modification of a capsule holder having an orifice plate fitted to the opening ends of the outflow air passages included in the outflow air passageway, cut in the same cutting surface as FIG. 8.

Referring now to FIG. 14, there is shown a third modification of the capsule holder employed in the inhalant medicator. In the first embodiment, the orifice plate 14 is installed or fitted onto the inflow-side axial opening end (the right-hand opening end) of the capsule holder 5. In lieu thereof, as appreciated from the third modification shown in FIG. 14, axial outflow passages 8A' and 8A' may be formed in the left half of the capsule holder 5 in such a manner as to axially extend from the respective radially-extending pin insertion channels 8B, 8B, and additionally an orifice plate 14', having orifices 15' and 15' of a flow passage area less than the flow passage area of the through hole H pricked in the capsule K and less than a flow passage area of the axial outflow passage 8A', may be installed or fitted onto the outflow side axial opening end (the left-hand opening end) of the capsule holder 5. Moreover, in the third embodiment shown in FIGS. 9 through 11, two different sizes, namely a small-diameter orifice 37 and a large-diameter orifice 38 are exemplified as an orifice plate 36 having a plurality of orifices of different orifice diameters. In order to accurately adjust both the flow velocity and the flow rate of air flowing through the interior of the capsule K during medication, an orifice plate having orifices of three different orifice diameters may be used. Also, an orifice plate having orifices of four or more different orifice diameters may be used to more accurately adjust the flow velocity and the flow rate of the air flowing through the capsule.

While the foregoing is a description of the preferred embodiments carried out the invention, it will be understood that the invention is not limited to the particular embodiments shown and described herein, but that various changes and modifications may be made without departing from the scope or spirit of this invention as defined by the following claims.

Industrial Applicability

As set forth above, an inhalant medicator made according to the invention is useful for the purpose of stably reliably dispersing granulated medicines, while satisfactorily keeping a specified flow rate and a specified flow velocity of air flowing through the interior of a capsule pierced during medication. Also, the inhalant medicator of the invention is useful for the purpose of efficiently prescribing granular medicines toward within lungs of a patient during medication, irrespective of physical properties of the granular medicines and/or the difference of vital capacity between an adult and a child (or weak or strong chests).

What is claimed is:

1. An inhalant medicator comprising:

a medicator body formed at one axial end with a capsule housing area and at another axial end with an inhalant port;

an inflow air passageway having an inflow passage extending in an axial direction of the medicator body and a first pin insertion channel extending in a radial direction of the medicator body for communicating the capsule housing area with ambient atmosphere;

an outflow air passageway having an outflow passage extending in the axial direction of the medicator body and a second pin insertion channel extending in the radial direction of the medicator body for communicating the capsule housing area with the inhalant port;

a boring tool having pins insertable into the first and second insertion channels and adapted to prick holes in a capsule accommodated in the capsule housing area with the pins; and an orifice plate located along one of the inflow and outflow air passageways, the orifice plate having a plurality of orifices formed therein and at least two of the orifices having flow passage areas different from each other, the flow passage area of each of the orifices being less than a flow passage area of each of the first and second insertion channels and less than a flow passage area of an other of the inflow and outflow air passageways.

2. The inhalant medicator as claimed in claim 1, wherein the medicator body has an axial auxiliary air passageway axially penetrating the medicator body in a circumferentially spaced relationship with both the inflow and outflow passages, and an auxiliary orifice is formed in the orifice plate for adjusting a flow passage area of the auxiliary air passage.

3. The inhalant medicator as claimed in claim 1, further comprising a support plug fitted to the medicator body and having a support shaft partly inserted into the capsule housing area for supporting the capsule by an inside end thereof and for rotatably supporting the orifice plate by an outer periphery thereof to selectively communicate at least one of the orifices with the first air passageway depending on physical properties of powdered and granular medicines stored in the capsule.

4. The inhalant medicator as claimed in claim 1, wherein the orifice plate is provided upstream of the capsule housing area.

5. The inhalant medicator as claimed in claim 1, wherein the orifice plate comprises a disc-shaped orifice plate formed at its central portion with a support hole through which the support shaft is partly inserted into the capsule housing area, and at least one of the orifices of the disc-shaped orifice plate is communicated with the first air passageway by rotating the disc-shaped orifice plate about the support shaft.

6. The inhalant medicator as claimed in claimed 5, wherein the disc-shaped orifice plate is operated between at least a first inhalation mode and a second inhalation mode by changing a combination of the orifices communicated with the first air passageway by rotary motion of the disc-shaped orifice plate, the first inhalation mode at which a relatively small-diameter orifice of the orifices is selected to increase a flow velocity of air flowing from the inflow air passageway via an interior of the capsule toward the outflow air passageway, and the second inhalation mode at which a relatively large-diameter orifice of the orifices is selected to decrease the flow velocity of air flowing from the inflow air passageway via the interior of the capsule toward the outflow air passageway.

7. The inhalant medicator as claimed in claim 6, wherein the medicator body has an axial auxiliary air passageway axially penetrating the medicator body in a circumferentially spaced relationship with both the inflow and outflow passages, and the disc-shaped orifice plate having a plurality of auxiliary orifices formed therein and having flow passage areas different from each other, the flow passage area of each of the auxiliary orifices being less than the flow passage area of each of the first and second insertion channels and less than the flow passage area of the second air passageway, and wherein a combination of the auxiliary orifices communicated with the axial auxiliary air passageway is changed by rotary motion of the disc-shaped orifice plate.

* * * * *